United States Patent [19]

Kleinberg

[11] Patent Number: 4,668,057
[45] Date of Patent: May 26, 1987

[54] COUNTER-BALANCING MICROSCOPE ASSEMBLY

[76] Inventor: Larry K. Kleinberg, 4401 Moorpark Way, #109, Toluca Lake, Calif. 91602

[21] Appl. No.: 738,240

[22] Filed: May 28, 1985

[51] Int. Cl.$^4$ .................... G02B 21/22; G02B 21/24; G02B 21/06
[52] U.S. Cl. .................... 350/515; 350/522; 350/528
[58] Field of Search ............ 350/507, 521, 522, 514, 350/515, 516

[56] References Cited

U.S. PATENT DOCUMENTS

| 3,891,301 | 6/1975 | Heller | 350/522 |
| 4,003,628 | 1/1977 | Halperin | 350/521 |
| 4,339,100 | 7/1982 | Heller et al. | 350/507 |

FOREIGN PATENT DOCUMENTS

| 0158318 | 12/1981 | Japan | 350/507 |
| 2113418 | 8/1983 | United Kingdom | 350/507 |

Primary Examiner—John K. Corbin
Assistant Examiner—Vincent J. Lemmo
Attorney, Agent, or Firm—Harness, Dickey & Pierce

[57] ABSTRACT

A microscope for use in all surgical disciplines, without need for ordinary or special tools, comprising an assembly of microscope, illumination module (magnification changer), fiber optics cable to the module, a mechanical assembly to which they are connected, means for focusing the microscope, means for mounting such assembly of elements to a fulcrum axis through the mechanical assembly, and a tilt-axis adjustable counterweight to balance the assembly, with or without addition or removal of elements, all operatively mounted to a support arm. A second adjustable counterweight is provided to prevent lateral or transverse tipping of such assembly when laterally extending accessories (e.g., observer's tube assembly) are added or removed. The mechanical assembly includes tension controls to change tilt of the microscope about the support arm, with the tilt-axis counterweight being accordingly adjusted. The support arm is mounted to a mounting member of a ceiling, wall or other counterweight stand, either directly or through an angle coupling. The support arm's position is swingable through an 180° arc, and when so swung, the noted mounting means is swung 180° about the fulcrum axis so that the microscope et al elements and first counterweight means remain in the same relative positions for use in surgical procedures. A safety latching system on the focusing means sub-assembly prevents fall-out of the weighted microscope et al elements from the mounting means should the tension controls be relaxed too much.

16 Claims, 19 Drawing Figures

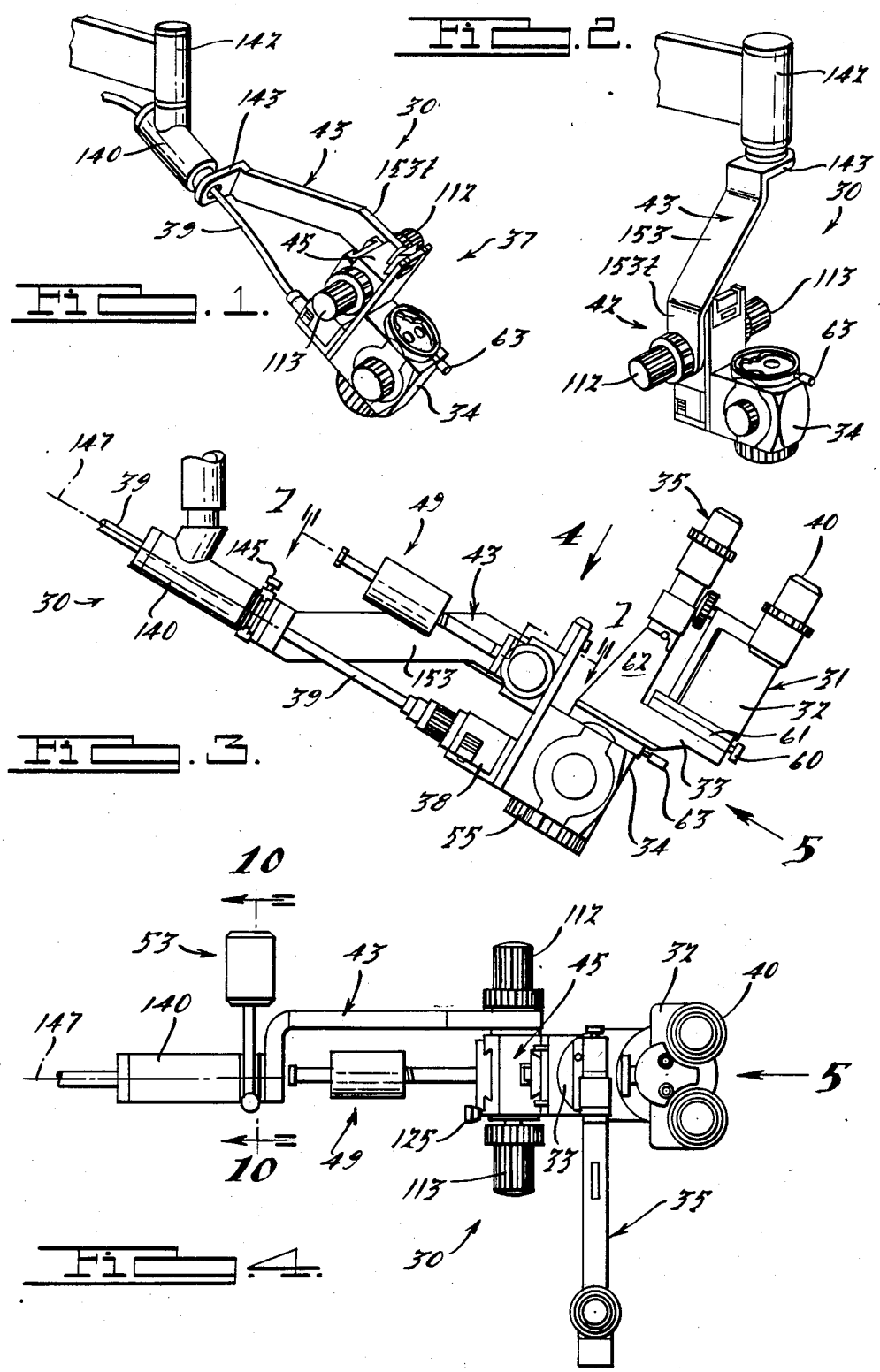

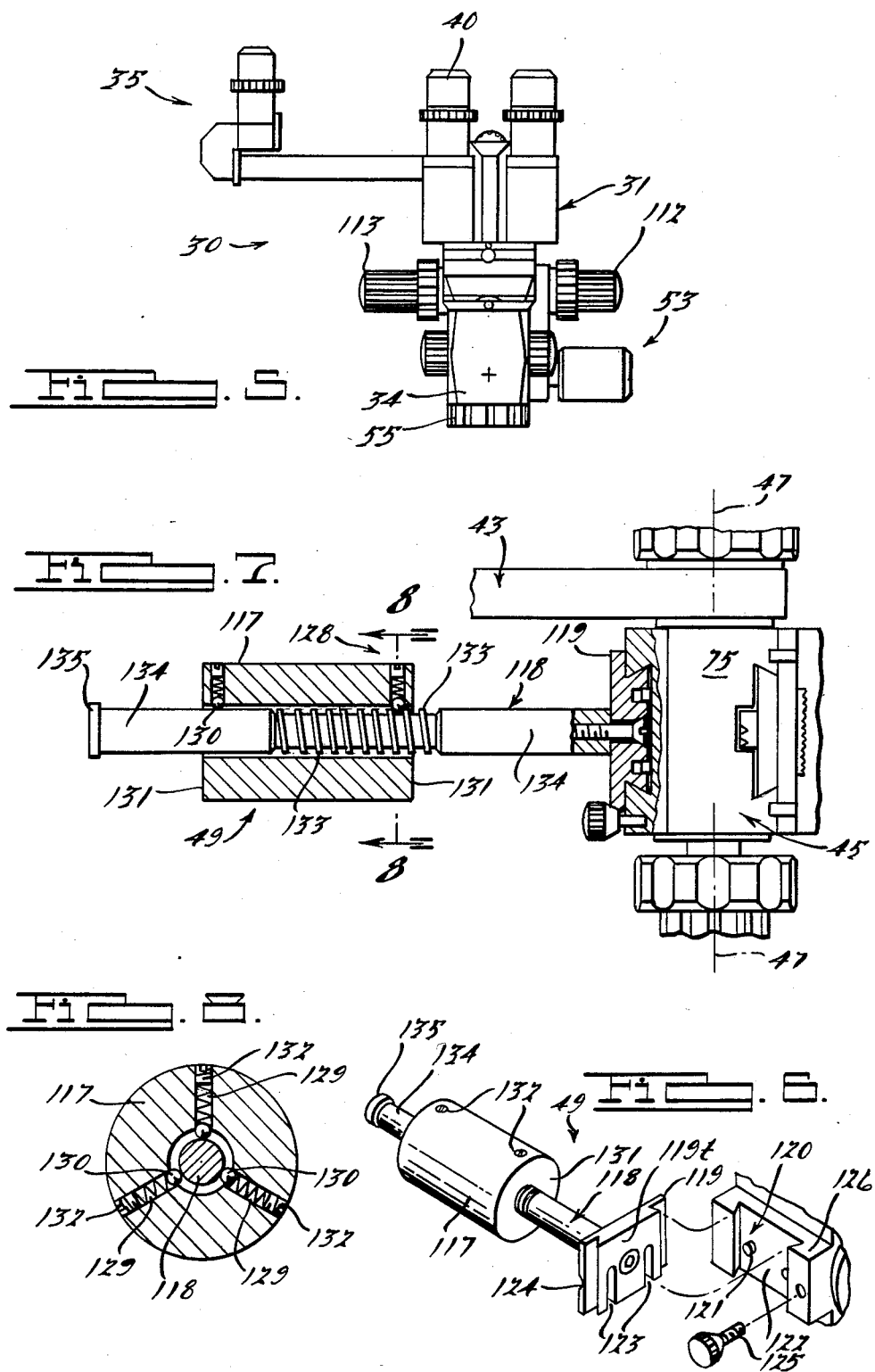

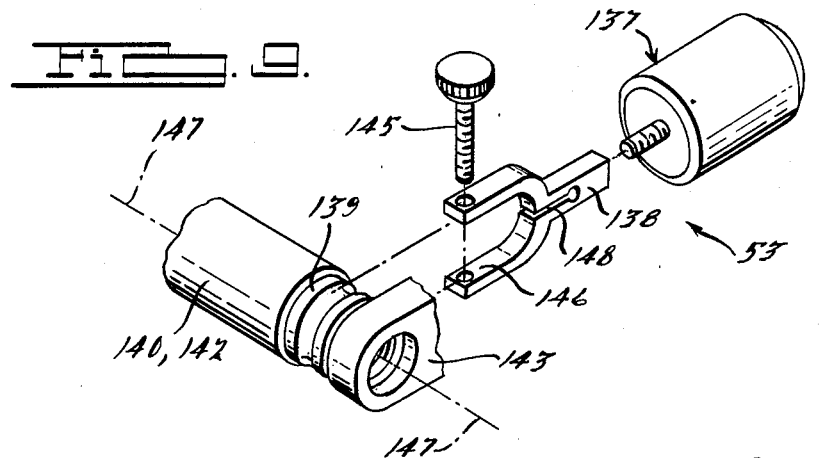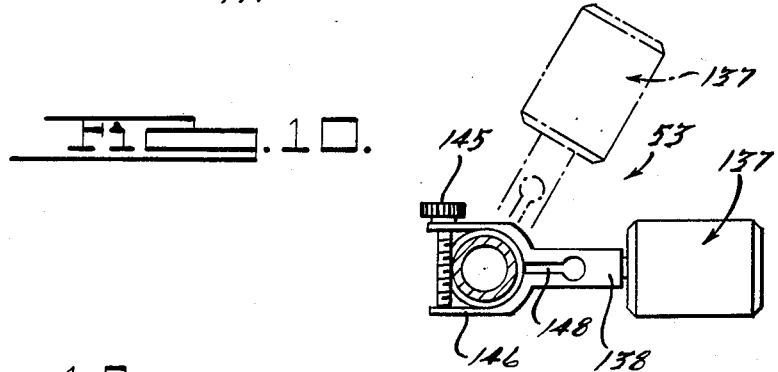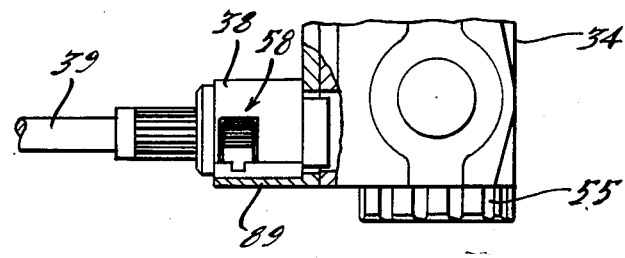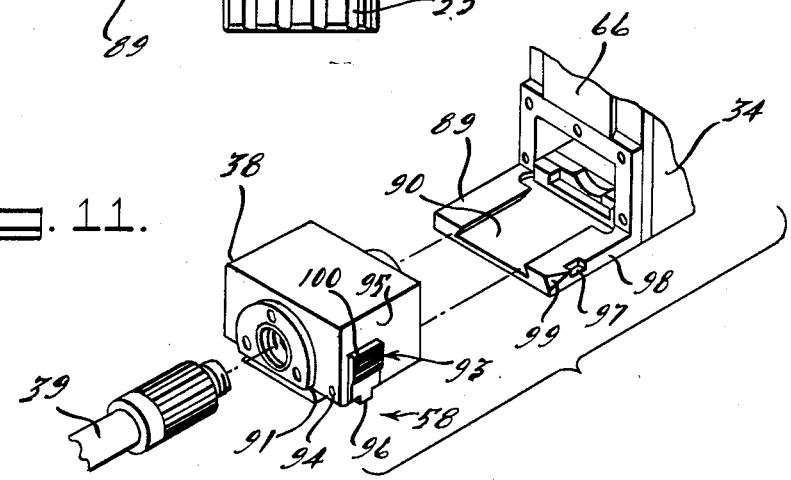

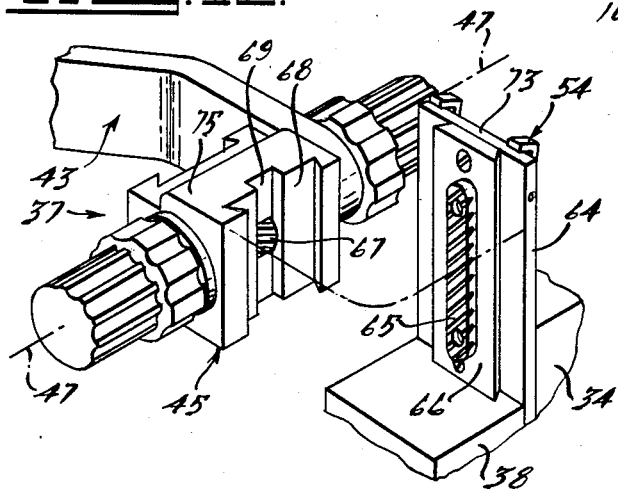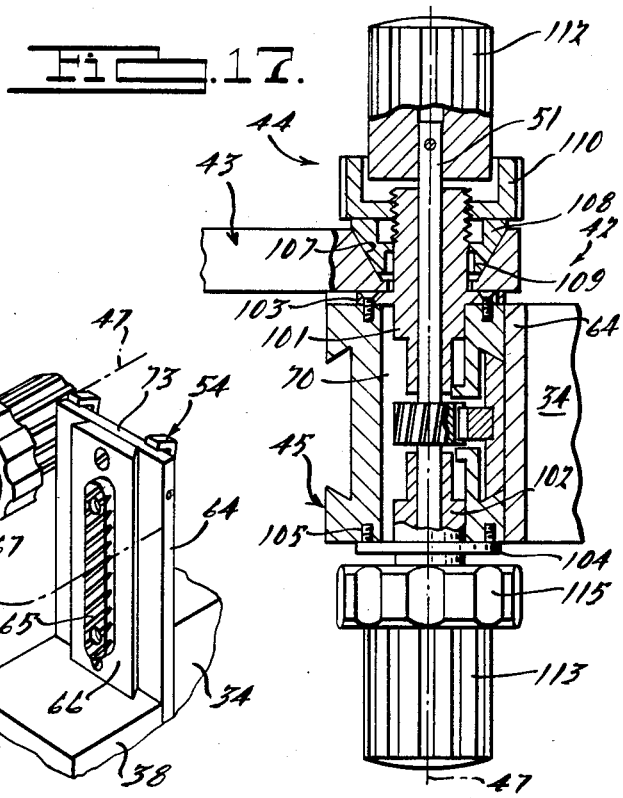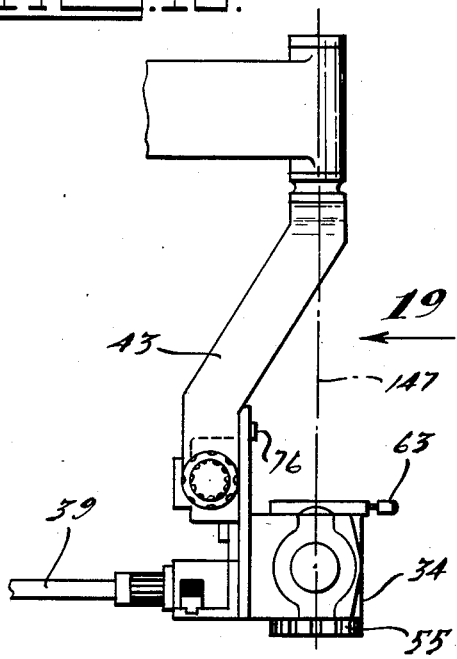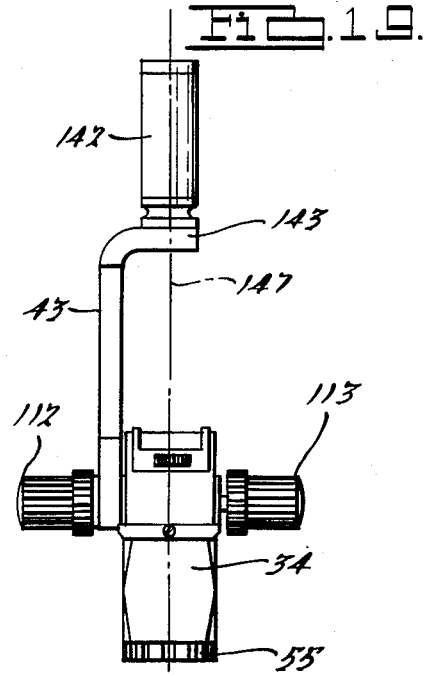

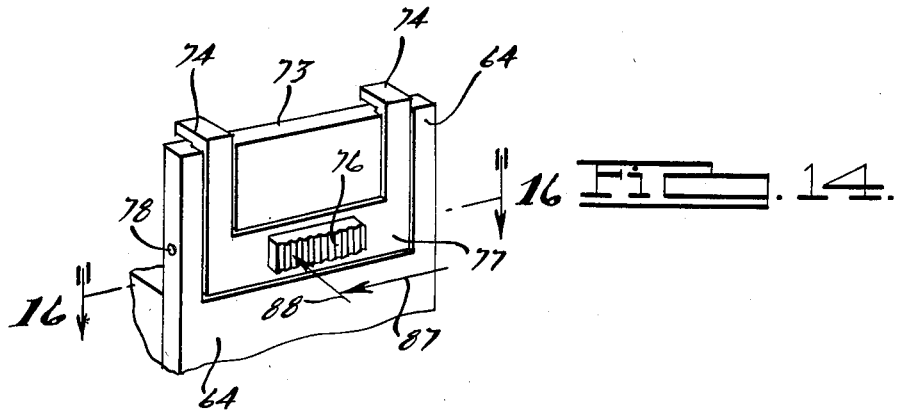
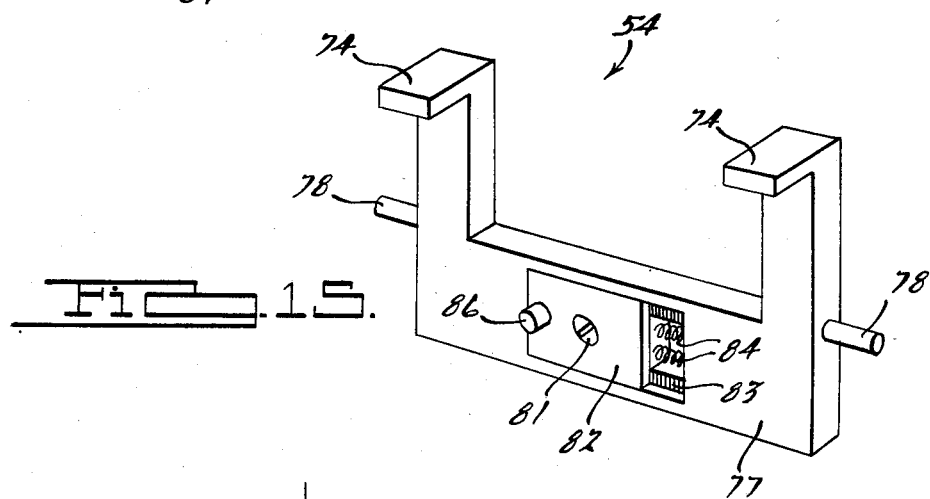
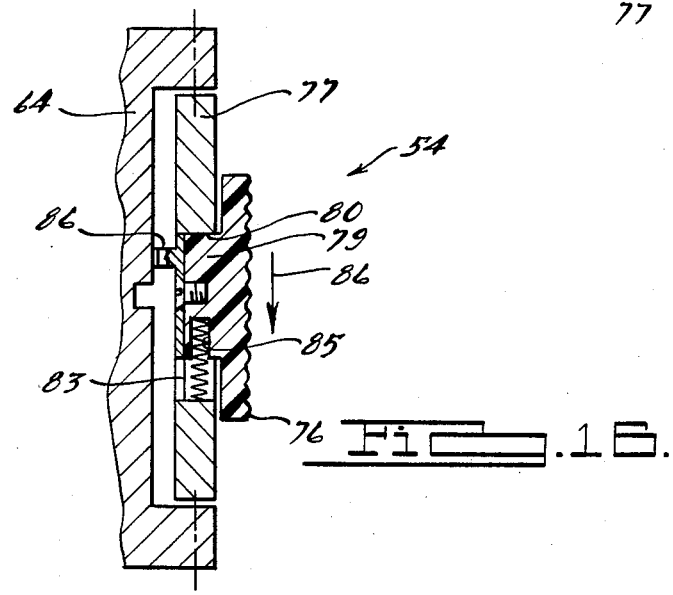

COUNTER-BALANCING MICROSCOPE ASSEMBLY

TECHNICAL FIELD

This invention relates to microscope assemblies, and in particular, to one for use in surgical disciplines though not limited thereto.

DISCLOSURE OF THE INVENTION

A. Background

Surgical procedures to produce efficacious results in the treatment of patient tissue or the like sometimes required use of a microscope in carrying out the specific procedures to treat the tissue "under the knife", so to speak. The procedure requires visual contact by surgeon with the target area(s) which is(are) limited in size. The microscope provides a field of view for the surgeon to inspect, examine and treat or otherwise act upon such tissue. A versatile microscope is in order for use by the surgeon, one readily manipulatable, and movable about, all with control and ease of control, during the procedure. The subject matter of this invention accomplishes a universal versatility of use desired in all surgical disciplines today.

B. Problems in the Prior Art

A major disadvantage in utilization of present day surgical microscopes is that there is no one microscope which is adaptable for all surgical disciplines, without the need of ordinary mechanical or other tools for converting a microscope from one physical assembly to another for use in a different discipline. Time, money, and efforts to train doctors, nurses, or other technical personnel to make necessary changes with tools on present day surgical microscopes have been added burdens to achieve use of them in the various and all disciplines.

C. Advantages of this Invention

An advantage of this invention is the utilization of but one microscope assembly for all surgical disciplines or otherwise, without the necessity of tools for changing the physical mode of the microscope. Expenditure of extra money, time, efforts, and training on the part of personnel, is eliminated. In the utilization of the subject matter of this invention, it only is necessary to change relative positions of various components of the product or apparatus and adjusting their positions, with and by the features incorporated into it.

Other advantages in the operation, assembly and use of the features of such subject matter are self-evident upon a full and complete reading of this disclosure, description and drawing.

D. Brief Summary of the Invention

This invention is found in a microscope assembly, with or without accessories or attachments, that is utilized in surgical procedures of all kinds. FIGS. 1 and 2 illustrate the two physical modes by which utilization of the subject matter of this invention can be had for all surgical disciplines, For example, FIG. 1 is used by all disciplines, one example of which being otolaryngology, while FIG. 2 illustrates a physical mode for its use in ophthalmology (eye surgery).

The subject matter of this invention is incorporated within a microscope assembly including a microscope, an additional housing or casing by which one or more observer's tube assembly can be mounted to the assembly in general, an illumination module which changes the magnification of the object or target area being seen through the binoculars of the microscope (and observer's tube assembly), the module being operatively connected to the microscope, a fiber optics cable which transmits light to the illumination module, a mechanical assembly (more fully described hereinafter) providing, in part, tension controls for changing the tilt of the microscope and to which the above noted elements are operatively connected, a means for focusing a microscope mounted on a mechanical sub-assembly connected to the mechanical assembly, a means for mounting such assembly of elements to a fulcrum axis which extends through the mechanical assembly, and an adjustable tilt-axis counterweight to balance any assembly of elements being utilized at the moment, all of this being operatively mounted to a support arm coupled to a mounting member or the like. A second adjustable counterweight is provided to prevent lateral or transverse tip of such assembly of elements, when one or more laterally extending accessories (e.g., observer's tube assembly) are added or removed to the entire apparatus. The mechanical assembly includes tension controls (clutching means) manually adjustable by the operator or surgeon and by which tilting of the microscope about the support arm is accomplished and for focusing the microscope by raising it or lowering it in relation to the fulcrum axis. The support arm is mounted to a mounting member suitably connected to a ceiling, wall or other counterweight stand, either directly or through an angle coupling. The support arm's position is swingable through a 180° arc about the axis of of the mounting member. Further, the means for mounting the microscope is rotatable about a shaft coaxial with the fulcrum axis extending through the mechanical assembly. Thus, when the support arm's position is swung through its 180° arc, into a second physical mode for the apparatus, the indicated mounting means is likewise rotated 180° about the fulcrum axis with the advantageous result that the microscope remains in the same relative position for use by the operator or surgeon.

The construction of the assembly for one particular surgical discipline for eye surgery is such that the optical axis along which the target area is viewed and the axis about-which the apparatus is capable of rotating are coaxial, thereby maintaining a centering for the same field of view for the surgeon, although he is viewing the target area (the eyeball) from a different angle from time to time during use.

A safety latching scheme on the focusing means subassembly prevents fall-out of the weighted microscope et al elements from the mounting means should the tension controls in the mechanical assembly be relaxed too much.

E. Objects of the Invention

An object of this invention is to provide for a novel and non-obvious microscope assembly.

Another object of this invention is to provide for a microscope assembly on one single support arm.

Another object of the invention is to eliminate the need of tools to convert or change a microscope on a support arm from one physical operative mode to another physical operative mode.

A further object of this invention is to achieve an adjustable balance for the microscope assembly when a change in tilt about the support arm is made, and or when a change in the addition or removal of accessories or attachments is made, either in relation to a tilt axis or a tip axis for the assembly.

Another object of this invention is to provide a microscope or other assembly which can have its physical position changed about a support arm thereof and by which the microscope remains in the same relative position for efficacious use in different procedures, surgical or otherwise.

Another object of this invention is to provide counterweight means which provides both fine or rough adjustment in counterbalancing a change in a moment arm developed about tilt or tip axes and brought about by addition or removal of weighted elements or components, or by deliberate changing of the tilt of the apparatus.

A further object of this invention is to provide an interchangable illumination module for a microscope assembly.

A still further object of the invention is to provide a safety scheme which prevents fall-out of the microscope and other elements from the assembly either during the course of changing from one physical mode to another physical mode, thus eliminating danger of damage or injury, or during a relaxed tension on controls for tilting or focusing the microscope.

Another object of this invention is to provide the same field of view through the microscope although its assembly is rotated about a generally vertically oriented axis of support.

These and other objects and advantages of the invention will become apparent upon a full and complete reading of the following description, appended claims thereto, and the accompanying drawing comprising 19 FIGURES.

BRIEF DESCRIPTION OF THE DRAWING

FIG. 1 is a perspective view of an apparatus, some physical components not being included, embodying the invention.

FIG. 2 is a perspective view of the apparatus of FIG. 1 in a change-of-arm position, achieved without a tooled conversion to achieve such position.

FIG. 3 is a side elevational view of the apparatus of FIG. 1, but including physical components not shown in FIG. 1.

FIG. 4 is a view taken on the direction of arrow 4, FIG. 3.

FIG. 5 is a view taken in the direction of arrows 5 in FIGS. 3, 4.

FIG. 6 is an exploded, perspective view of a counterweight sub-assembly employed in the invention, shown in a different view than those of FIGS. 7, 8.

FIG. 7 is a view taken on line 7—7 of FIG. 3.

FIG. 8 is a view taken on line 8—8 of FIG. 7.

FIG. 9 is an exploded, perspective view of another counterweight sub-assembly employed in the invention.

FIG. 10 is an assembled view of the counterweight element of FIG. 9, an alternate position thereof shown in phantom.

FIG. 11 is an exploded, perspective view of an illumination module in tandom to its receiver mounted on the rear of a magnification housing, and a fiber optics cable in tandom to such module.

FIG. 12 is a side, partly sectional, view showing cable, module, and magnification housing of FIG. 11 assembled together.

FIG. 13 is a fragmentary perspective view of a rack-and-gear focusing mechanism in relation to a mechanical assembly for focusing and tilting a microscope, and a safety latching scheme for the microscope.

FIG. 14 is a fragmentary perspective detail of the latching scheme shown in FIG. 13.

FIG. 15 is a reverse view of the latching element in FIG. 14.

FIG. 16 is a view taken on line 16—16 of FIG. 14.

FIG. 17 is a cross-sectional view of the mechanical assembly shown in FIG. 13.

FIG. 18 is a side view of the perspective shown in FIG. 2.

FIG. 19 is a view taken along the direction of arrow 19 in FIG. 18.

DESCRIPTION OF BEST MODE OF THE INVENTION

Referring now to the FIGURES of the drawing wherein reference characters correspond to like numerals hereinafter, FIGS. 1-5 generally illustrate an embodiment of the invention which assembles together into one apparatus 30 or unitary product its subject matter. A microscope 31 is contained within its housing 32 which is mounted upon a casing 33 mounted upon a housing 34 containing a magnification changer. Casing 33 in this embodiment is constructed to provide optional mounting of an observer's tube assembly 35 should it be desired to do so. A means 37, FIGS. 1, 13, for controlling the focusing of microscope 31 is mounted to housing 34 for the magnification changer. An illumination module 38 is mounted to housing 34 for introduction of light, via a fiber optics cable 39, to the optical system (not shown) by which an observer through the binoculars 40 of microscope 31 (and tube assembly 35) observes the target area image or object. A mechanical assembly 42, FIGS. 2, 13, 17, hereinafter more fully described, is operatively connected to a support means 43, a means 44, FIG. 17, for controlling the degree of tilt for microscope 31 about support arm 43, and a means 45, FIGS. 1, 13, 17, for mounting microscope 31 to a side of a fulcrum axis 47, FIGS. 13, 17, coaxial with the axis of mechanical assembly 42 itself.

A first counterbalancing means 49 cooperates with weight of some aforementioned elements (and any other optionally mounted attachments or accessories), by balancing them to a desired degree of tilt about fulcrum axis 47, which also extends through support arm 43, and is operatively connected to mounting means 45 in opposing relation to some aforementioned elements. Mounting means 45 is operatively connected to mechanical assembly 42 in such a manner, more fully described hereinafter, that the former is rotatable on the latter. Mounting means 45 itself is universally rotated about a shaft 51 forming mechanical assembly 42, shaft 51 being coaxial with fulcrum axis 47. Thus, mounting means 45 is universally rotatable in relation to support means 43 to thereby maintain the same relative positions of counterweight means 49 and the aforesaid described elements located to the other side of such fulcrum axis 47 when apparatus 30 translates from the physical mode of FIG. 1 to that of FIG. 2.

A second counterweight means 53, FIGS. 9, 10 which controls tip (in a lateral or transverse direction) of an assembly of elements constituting the unitary product is mounted adjacent an end of support means or arm 43 which is opposite to the end at which mechanical assembly 42 is connected, and counterbalances the weight of any addition or removal of optional attachments or accessories adaptable to the product or apparatus 30, i.e., those added or removed having weight in a lateral sense or direction. The observer's tube assembly 35 is an example. In this embodiment, observer's tube assembly 35 extends laterally of a vertical plane (not shown) dividing the microscope's housing 32.

A safety-latch mechanism 54, FIGS. 14, 15, 16, is mounted on focusing control means 37, to prevent fallout of the latter (and any elements mounted thereto) from mounting means 45 should the tension controls in mechanical assembly 42 become too relaxed in relation to the latter's shaft 51.

An objective lens (not shown) is included in a retainer ring 55 suitably attached to housing 34 of the magnification changer.

Another latching means 57, FIGS. 11, 12, along with a means 58, such as a tongue-and-groove arrangement, provide the wherewithall to maintain operative connection between housing 34 for the magnification changer and any one of interchangeable modules 38. In more particularity, the microscope's housing 32 is suitably securedly mounted, in known manner, such as by a screw 60, FIGS. 2, 3, to an annular ring member 61 on casing 33 which has a matching circular dovetailing configuration to receive head 32. Similarly, the bottom of casing 33 is suitably securely mounted, in known manner, to the top of housing 34 by a like or similar means 63. Casing 33 includes an upraised housing configuration 62 at the top of which observer's tube assembly 35 is suitably and similarly securely mounted in known manner thereto. Tube assembly 35 extends laterally, FIG. 4, from generally the vertical plane (not shown) which divides housing 32.

The microscope (and observer's tube, likewise) is focused upon an image or target below the objective lens in retainer ring 55 by means of raising it and lowering it, along with housing 34. As shown more particularly in FIG. 13, a plate member 64 is suitably secured to one side of housing 34 and includes a mitered rack member 65 secured to a tongue 66. Rack member 65 cooperates with a pinion gear 67 suitably secured to shaft 51, FIG. 17, in mechanical assembly 42, upon introduction and receipt of tongue 66 in a complementing groove 68 formed in a block forming mounting means 45. Rack member 65 seats in a notch 69 into which gear 67 protrudes from a chamber 70 in mounting means 45 to make such cooperation, with the tongue-and-groove arrangement 66, 68 not interfering therewith, or vice-versa, FIG. 17.

Safety-latching scheme 54 is suitably pivotally mounted adjacent one terminal edge 73 of plate member 64, having a pair of spaced fingers 74 projecting past such edge 73 for abutting against one wall 75 of block or mounting means 45. This safety scheme is necessary in the operation of apparatus 30, when housing 34 is joined to mechanical assembly 42, as otherwise the former could travel free of or otherwise disengage from the latter by reason of free turning or rotating of shaft 51. Latch means 54 comprises, FIGS. 14, 15, 16, a slidable spring-loaded finger button 76 mounted on a latch member 77 pivotable as at 78. Button 76 includes an inner projection 79 which seats in an opening 80 in latch member 77, slidable thereacross, and is retained thereto by means of a screw 81 through a retaining plate 82 seated on flanges 83 formed about opening 80 on the back side of latch member 77. A pair of springs 84 mounted in corresponding bores 85 in projection 79 biases button 76 in one direction, the direction by which latching fingers 74 grasp edge 73 of plate member 64, FIG. 13. A pin, 86, FIG. 16, projects outwardly of retaining plate 82 to slide in a slot or groove in plate member 64, as button 76 is pushed in the direction of the arrow 87 shown in FIG. 14. As soon as pin 86 centers over a hole in plate member 64, then button 76 can be depressed in the direction of arrow 88, FIG. 14, as a result of pin 86 entering such hole, and latch member 77 pivots about 78 (which is one of two pins about which latch member 77 pivots). With such depression, latching fingers 74 are swung out of abutting disposition against wall 75, FIG. 13, of mounting means 45, thereby providing removal of plate member 64 and its rack 65 from engagement with such mounting means 45 and gear 67, when desired.

Below tongue 66, FIGS. 11, 12, an L-shaped receptacle 89 is suitably securedly mounted to housing 34, and includes a female dovetailing groove 90 for accepting a complementing male member 91 securely mounted to the underside of module 38. A latch means 93 (in and of itself being state-of-the-art construction) is pivotably mounted by means of a pin 94, FIG. 11, to one wall 95 of module 38, for locking module 38 to receptacle 89 and thus, to housing 34. Latch means 93 includes a downwardly depending lug 96 which cooperates with a complementing notch 97 in an edge 98 to maintain a locked mode for module 38 and housing 34. Lug 96 is spring-biased (not shown) downwardly, and as male member 91 is received by groove 90, a corner guide 99 pivots lug 96 about pin 94 in order to ride over edge 98 until it snaps into its seat in notch 97. A button 100 is provided in latch means 93 to pivot lug 96 about pin 94, away from notch 97 when module 38 is to be detached from receptacle 89. (Details of other construction for latch means 93 have been omitted, as this type of fastener is state-of-the-art teachings).

Fiber optics cable 39, FIGS. 11, 12, is suitably secured, such as by threading, to module 38, for providing light in the operation of apparatus 30, and extends in its opposite direction to a known source of illumination (not shown) therefor.

Turning now to FIG. 17, mechanical assembly 42 comprises rotatable shaft 51 supported by a pair of spaced bearings or bushings 101, 102 having annular portions 103, 104, respectively, in between and to which mounting means 45 is secured, such as by screws 105. Bushing 101 extends through a tapered hole 107 adjacent one end of support arm 43, while a frustum member 108 mounts such bushing 101, being keyed thereto as at 109, and being disposed in hole 107 for complementary abutment to the latter's taper. An annular ring 110 is threaded to bearing 101 for abutment and adjustment relative to frustum member 108. Tightening of ring 110 against frustum member 108 causes frictional gripping thereof with support arm 43, thus stationarily positioning mounting means 45 relative to such arm. Full loosening of ring 110 provides universal rotation of mounting means 45 and mechanical assembly 42 (in general) relative to support arm 43.

Knobs 112, 113 are pinned to rotatable shaft 51 for manually turning gear 67, the rotation of shaft 51 controlling focusing for microscope 31 as the latter raises and lowers relative to fulcrum axis 47 and mounting means 45.

A second annular ring 115 is threaded (not shown) to the other bearing member 102 which in turn, although not illustrated in FIG. 17, includes state-of-the-art design and construction for a clutch braking assembly against shaft 51. For example, longitudinally disposed slots separate say, four (4) tapering bearing portions of member 102 under corresponding ones of which braking shoes, mounted over and on shaft 51, are disposed. Tightening of ring 115 (towards mounting means 45) produces frictional engagement of the shoes upon shaft 51. Thus, a conventional clutching means is provided for shaft 51 whereby a particular point on rack 65 is held to gear 67 secured to shaft 51, and to thereby focus microscope 31. Loosening of ring 115 enables shaft 51 to rotate, by means of knobs 112, 113, thereby raising or lowering microscope 31.

Counterweight means 49, FIGS. 6, 7, 8, balances the weight of apparatus 30 to the opposing sides of fulcrum axis 47, in a tilt plane through such axis 47 for the microscope, and for any tilted position desired for microscope 31 relative to support arm 43. Means 49 detachably mounts to mounting means 45 in opposing relationship to such indicated weight, and comprises a sleeve 117 mounted along a cylindrical stem 118 which is suitably secured to a member 119 having a tongue 119t which cooperatively engages a groove 120 in mounting member 45. A pair of limit pins 121 projects from the groove's base 122 for cooperative engagement with a corresponding pair of slots 123 extending upwardly from a bottom edge of tongue 119t. A small arcuate recess 124 is formed in an edge of member 119, to cooperate with the head of a screw 125 threaded to one of the tracks 126 forming groove 120, to prevent fall-out of tongue 119t from mounting member 45 when in an upside down disposition, i.e., from that shown in FIG. 6. As seen in FIGS. 7 and 8, two sets of detent means 128, each having three radially-extending bores 129 equally distant from one another and in which spring-biased ball members 130 are disposed, are mounted in sleeve 117, each set disposed preferably adjacent a corresponding end face 131 for sleeve 117. A set screw 132 holds each spring and ball member in place in its corresponding bore. The ball members 130 are adapted to engage the race of a helically wound threaded portion 133 of sleeve 117, however, it is to be noted that the ball members in both sets of detent means 128 do not engage such helically wound threaded portion simultaneously. One set engages a corresponding stem portion 134 when the other set engages threaded portion 133. A cap 135 is suitably secured to the end stem portion 134 of stem 118 to prevent slip off of sleeve from stem.

The second counterweight means 53, FIGS. 9, 10, 3, prevents tipping of apparatus 30 and provides balance for apparatus 30 about a tip axis when an attachment(s) or accessory is added or removed for utilization in the operation of the apparatus. For example, when observer's tube assembly 35 is added or removed. The tip axis for apparatus 30 lies in the plane perpendicular to the drawing sheet and passing through the arrow "5" shown in FIG. 4. Means 53 comprises a weighted sleeve 137 suitably securely mounted, such as by threaded screw, to the yoke of a forked member 138 itself attachable upon the annular groove 139 formed in a mounting member or coupling 140, 142, FIGS. 1, 2, immediately adjacent an apertured lug member 143 on support means 43 and to which member 143 such coupling is threaded. A screw 145 holds forked member 138 to groove 139, and its threading to leg 146 of forked member 138 tightens and secures counterweight means 53 in a desired position about a support axis 147 for apparatus 30, by reason of a slot 148 formed in the yoke of forked member 138 closing upon itself as screw 145 is tightened.

It may be noted that the constructions or designs of counterweight means 49, 53 are interchangeable in their two locations of apparatus 30, should this be desired to be done. I.e., weighted sleeve 137 could be fixedly mounted to stem 118 while sleeve 117 and its detent means 128 and helically threaded portion 134 can be mounted on forked member 138. Or, either counterweight means could be used at both locations at the same time.

It is to be noted that support means or arm 43 includes a length 153 disposed in an angular fashion to terminal portion 153t, FIGS. 1, 2. In this embodiment then, the support axis 147 and the fulcrum axis 47 do not intersect. However, this angular disposition 153 provides for axial imposition of axes 147 and 47, one upon the other, in the FIG. 2 operational mode. The advantage of these co-axially aligned axes becomes apparent in the operation of the FIG. 2 mode.

It should be understood that observer's tube assembly 35 represents any attachment or accessory, one or more, mounted to either side of the vertical plane dividing the microscope's housing 34 in half. This vertical plane can be described as being perpendicular to the plane of the drawing and passing through the arrow identified as "5" in FIG. 4. Thus, counterweight means 53 balances any such addition or removal thereof to apparatus 30, by angularly displacing it about axis 147 and tightening it to groove 139 by using screw 145.

Coupling 140, FIG. 1, provides an angular orientation for apparatus 30 and which is beneficial in orientation of apparatus 30 for all surgical disciplines except for that relating to eye surgery. The FIG. 2 mode provides utilization of apparatus 30 in the particular discipline ophthalmology (eye surgery). One of the unique advantages of this invention is that apparatus 30 can be utilized in all surgical disciplines, in either mode of operation illustrated by FIGS. 1 and 2, without the need of tools either to change the apparatus or its elements around or to eliminate some elements. Lug member 143 simply is threaded either to angular coupling 140 which in turn has been suitably secured to post 142 or is threaded directly to post 142.

Operation

In the FIGS. 1, 3 physical mode, to change the tilt of microscope 31 mounted on housing 34 and other elements affected by such movement, the tension of ring 110, FIG. 17, on clutch means 44 (frustum 108) is relaxed sufficiently, so that mounting means 45 to which housing 34 is mounted can rotate about axis 47, i.e., about support arm 43, by turning knob 113 when the tension on shaft 51 by ring 115 is tight. It is not a full relaxation or loosening of ring 110 that is required to produce a desired change in tilt, as frustum 108 can slightly frictionally engage the hole taper in support arm 43 during the tilting motion. Housing 32 or some other depending element thereto can be grasped also, to cause change in tilt. A small change in tilt requires but a fine adjustment of counterweight means 49, in order to maintain balance of weighted elements to the other side of fulcrum axis 47. Should the microscope be rotated clockwise, as seen in FIG. 3, with change in the moment arm between it (and other affecting elements) and fulcrum axis 47, sleeve 117 is rotated on stem 118 towards cap 135. If rotated counter clockwise, sleeve 117 is rotated on stem 118 towards mounting means 45.

When a major change or degree in tilt is desired, requiring a relatively large angular movement of microscope about fulcrum axis 47, with such movement accomplished, sleeve 117 can be adjusted roughly to its new position by pushing it linearly along stem 117. The threads of helically wound threaded portion 133 are overridden by the resiliency of ball detent means 128, i.e., ball members 130 compress against their springs in bores 129 as they progress over the threads of portion 133. Thereafter, a fine adjustment to re-establish balance in the new tilt of the microscope is made by rotating sleeve about stem. And retaining cap 135 prevents any ball 130 from falling out of its bore 129, since sleeve 117 itself is stopped in movement by such cap.

A focusing or re-focusing of microscope 31 is provided by relaxing sufficiently the tension of ring 115, i.e., the affected brake shoes are released from shaft 51 so that it can be rotated, by either or both knobs 112, 113, to thereby cause gear 67 to rotate, thereby raising and lowering plate member 64. This movement of plate member 64 changes the position of the objective lens in retainer ring 55 to its new or different position which focuses the microscope to the eyes of the operator through binoculars 40. Upon such focus, knob 115 again is tightened (towards mounting means 45), the affected brake shoes frictionally grabbing shaft 51, to thereby stationarily position plate member 64, and thus also the objective lens 55 at the correct focusing position.

It may be noted that a fine adjustment of a counterweight means 49 in the changed tilting position for the microscope may not be undertaken until after the focusing step is completed, and is available by at least one set of detent means 128 always engaging threaded portion 133.

The addition or removal of an observer's tube assembly 35 requires re-positioning of counterweight means 53, illustrated in phantom in FIG. 10, about support axis 147, in order to re-establish balance for apparatus 30 about support axis 147. Screw 145 is loosened sufficiently to provide rotation of forked member 138 in and about groove 139 to re-establish such balance. It is to be noted that counterweight means 53 is not restricted to any degree about support axis 147, in the re-establishment of balance.

In the above illustration of operation, illumination from a source of light is being transmitted through fiber optics cable 39 into illumination module 38 to which it is connected, and thence into the magnification chamber within housing 34, and through the objective lens in retainer ring 55, so that the operator or surgeon has illuminated sight of a target area or some object in the field of view to which focus is being made in the operation of apparatus 30.

With regard to the FIG. 2 mode of operation, essentially the same steps indicated above are taken. However, knobs 112, 113 are interchnged relative to the hands of the surgeon or operator. Such relative positions for these knobs are clearly observable in FIGS. 1 and 2. This change of position of knobs 112, 113 occurs by removing coupling 140 and connecting lug 143 directly to coupling 142, rotating or swinging support means 43 through an arc of 180° about support axis 147, and rotating mounting means 45 through a 180° arc about shaft 51 in order that housing 34 remains in its same position as it was in the FIG. 1 mode of operation.

It is to be noted that notch 124 and screw 125, FIG. 6, constitute a safety feature during the non-tooled conversion from the FIG. 1 to the FIG. 2 mode of operation. Were the nurse, doctor or other technician to fail to securely tighten screw 125 into track 126, thereby securing member 119 to mounting means 45, its cooperation with notch 124 prevents fall-out of member 119 when mounting means 45 is rotated 180° on shaft 51 (for the FIG. 2 mode), and thus, counterweight means 49 from mounting means 45. In the FIG. 1 mode, spaced pins 121 themselves limit the extent of position of member 119 in groove 120, preventing any fall-out whatsoever.

An additional advantage in the FIG. 2 mode of operation is that the support axis 147 and the optical axis for the microscope are coaxial. As support means 43 is rotated about support axis 147 in the FIG. 2 mode, when desired by the surgeon, the optical axis during such rotation remains centered in the field of view, irrespective of further tilting or tipping of the assembly.

Assembly

Assembly of the aforesaid elements is apparent from the above description, however, in one assembly thereof, briefly, after fabrication of such elements, gear 67 is press fit to shaft 51, after which they are introduced into chamber 70 of block member forming mounting means 45. Chamber 70 is provided with a bore diameter such that shaft and gear can be inserted therein and then causing gear 67 to project past the bottom or base of notch 69, FIG. 13. In such position of projection for gear 67, bushings 101, 102 are mounted to shaft 51 and screws 103, 105 then secure together mounting means 45 and bushings 101, 102, as shown in FIG. 17.

Bushing 101 is thrust through hole 107 in arm 43, and frustum member 108 mounted thereon, being keyed thereto at 109. Ring 110 is threaded to bushing 101 and knob 112 pinned to shaft 51.

Ring 115 is threaded to bushing 102 after the brake shoes (not illustrated) are inserted between bushing 102 and shaft 51, and thereafter knob 113 is pinned to shaft 51.

Button 76 is mounted into opening 80 of latch member 77, with springs 84 previously installed in bores 85. Retaining plate 82, with its pin 86, is then mounted on flanges 83 and secured to button 76 by screw 81. Latch member 77 is then pinned, by 78, to spaced extensions of plate 64, as shown in FIG. 14.

With receiver 89, FIG. 11, magnification housing 34, tongue 66 and plate member 64 suitably secured together in their sub-assembly illustrated in FIG. 13, tongue 66 and rack 65 are mounted correspondingly to notch 69 and groove 68, by first pivoting fingers 74, via button 76, and then introducing the tongue's end at edge 73 of plate member 64 into groove 68. With edge 73 caused to rise above wall 75 of the block member of mounting means 45, button 76 is released and fingers 74 are now capable of abutting wall 75.

Illumination module 38, FIG. 11, is received by receiver 89, via cooperating tongue 91 and groove 90, and locked in position via depression 96 seated in notch 97. Fiber optics cable 39 is threaded into module 38 as shown and suggested by FIGS. 12, 13. Ring 55 (with its objective lens) is suitably mounted to housing 34. Observer's tube assembly 35 is mounted to casing 33, and microscope 31 with its binoculars 40 are mounted to casing 33 after the latter has been mounted to housing 34.

Sleeve 117 is mounted on stem 118, cap 135 therafter secured to end stem portion 134, one set of balls 130 engaging the races of threaded portion 133. The other stem portion 134 was previously secured to member 119, FIG. 7, after which tongue 119t is detachably mounted to groove 120 formed in mounting means 45.

Suitable materials, such as metal and plastic, form the substance of the aforementioned described elements, all of which are fabricated in known manner and processes.

It now should be apparent that the specific natures of the aforesaid described elements, i.e., those of the microscope, casing, observer's tube assembly, magnification chamber housing, illumination module and fiber optics cable, are not essential to or contemplated within the concept behind the disclosure of the invention. For example, illumination module 38 contains the optical element and system thereof and which function to focus the illumination transmitted by fiber optics cable 39. The details of construction are not necessary here. However, the inventive concept contemplates the removeability and interchangeability of a plurality of modules 38 so that different optical focusing elements in different modules bring the illuminating input from the cable to the correct field size. Such optical focusing elements are available in different focal lengths to control field size. Thus, the concept of the invention contemplates the interchangeability and removeability of module 38 in order to introduce different focusing elements which are essential to utilization of the assembly in distinct surgical disciplines but without the necessity of conversion of the subject matter of the invention with tools. Advantages obtained are non-retrofitability aspects to such subject matter and the elimination of the need of taking the microscope assembly to a facility for changing to another size. The technician makes what changes are necessary immediately, quickly and easily.

The contemplation of the invention also includes the unique manner by which support means or arm 43 provides support for the subject matter in any of or all of the surgical disciplines undertaken. With its interchangeable arm position (the 180° rotation thereof), the invention concept contemplates the unique feature of universal rotatability of mounting means 45 on shaft 51, coupled to the other elements fashioning mechanical assembly 42. Also, the safety feature of the notch-and-screw, FIG. 6, by which counterweight means 49 does not accidentally fall out in the rotation of mounting means 45. Further, that the entire assembly product or unit is capable of revolving around the optical center of the objective lens in retainer ring 55, in the FIG. 2 mode, while maintaining the visual center on such lens, the support axis of means 43 being coaxial with the optical center of such lens.

Industrial Applicability

The subject matter of the invention finds it applicability in the medical field of arts, particularly to use in surgical disciplines, procedures and practices.

In accordance with the patent statutes, I have described the principles of construction and operation of my counterbalancing microscope assembly, and while I have endeavored to set forth the best embodiment or mode of carrying out the invention, it should be understood that changes may be made within the scope of the following claims without departing from the spirit of my invention.

I claim:

1. An assembly for a microscope comprising
a first housing,
a microscope housing operatively connected to said first housing,
a rotatable shaft coaxially mounted to a fulcrum axis, tilt clutch means and focus clutch means mounted on said shaft,
a gear secured to said shaft,
means including a rack disposed to one side of the fulcrum axis, said rack cooperatively engaging said gear,
said first housing securely mounted to said means including a rack,
means for mounted said means including said rack to said shaft,
said tilt clutch means and focus clutch means secured to said mounting means,
said focus clutch means operable upon said shaft to raise and lower said means including said rack and thereby operable on the focusing of the microscope in its housing,
said tilt clutch means adapted to be operable upon a support means for the assembly and thereby change the tilt of the microscope in its housing about the support means.

2. The assembly of claim 1 including
a support means having
(a) its one terminal end adapted for coupling to a mounting member having a support axis for the assembly,
(b) means at its other terminal end forming an opening,
said tilt clutch means operatively connected to said support means at such opening, and
an adjustable counterweight means mounted to said mounting means to the other side of the fulcrum axis.

3. The assembly of claim 2 including
a mounting member,
said support means operatively connected at its one end to said mounting member, and
a second adjustable counterweight means mounted upon said mounting member to balance said assembly in a lateral sense, said second adjustable counterweight means adjustable about the support axis for the assembly.

4. The assembly of claim 3 wherein said mounting member includes
a groove mounted in said mounting member,
a yoked forked member having spaced legs in alignment with said groove, and
a means for tightening said legs to said mounting member.

5. The assembly of claim 4 wherein said tightening means comprises
a screw member mounted to and across said spaced legs and having a shank engaging said groove to hold said forked member thereto, and being threaded to at least one of said legs to secure said forked member to said mounting member.

6. The assembly of claim 5 wherein said forked member includes a slot at its yoke.

7. The assembly of claim 4 or claim 5 or claim 6 wherein said second adjustable counterweight means is secured to the yoke of said forked member.

8. The assembly of claim 1 or claim 2 or claim 3 including
an illumination module mounted to said means including a rack and being operatively connected to said first housing.

9. The assembly of claim 8 including
a safety means mounted on said means including a rack for abutting said mounting means to prevent disengagement between the two.

10. The assembly of claim 9 wherein said latch means pivots to disengage said means including a rack from said mounting means.

11. The assembly of claim 8 including
a fiber optics cable operatively connected to said illumination module.

12. The assembly of claim 11 including
a safety latch means mounted on said means including a rack for abutting said mounting means to prevent disengagement between the two.

13. The assembly of claim 11 wherein said illumination module is interchangeable for another.

14. The assembly of claim 1 or claim 2 or claim 3 including
a safety latch means mounted on said means including a rack for abutting said mounting means to prevent disengagement between the two.

15. The assembly of claim 14 wherein said latch means pivots to disengage said means including a rack from said mounting means.

16. In an assembly for a microscope and attachments therefor, the improvement comprising
a support means having a first terminal portion and a second terminal portion and defining a support extending through the said first terminal portion, and defining a support axis extending through the said first terminal portion,
means for mounting a microscope and attachments therefor to both sides of a fulcrum axis,
a rotatable shaft axially aligned with such fulcrum axis,
said mounting means mounted and rotatable about said shaft,
said shaft within said mounting means adapted for operative focusing connection to a microscope on one of the sides to the fulcrum axis, said mounting means adapted for an attachment to said second terminal portion of said support means on the other one of the sides to the fulcrum axis,
focus clutch means for clutching said mounting means to said rotatable shaft,
tilt clutch means for clutching said rotatable shaft to said second terminal portion of said support means,
said focus clutch means and said tilt clutch means mounted on said shaft, said focus clutch means operable upon said shaft to frictionally inhibit rotation of said shaft and thereby inhibit said focusing connection to said microscope, said tilt clutch means operable upon said support means to frictionally inhibit change in the tilt of the microscope about said support means.

* * * * *

UNITED STATES PATENT AND TRADEMARK OFFICE
CERTIFICATE OF CORRECTION

PATENT NO. : 4,668,057

DATED : May 26, 1987

INVENTOR(S) : Larry K. Kleinberg

It is certified that error appears in the above-identified patent and that said Letters Patent is hereby corrected as shown below:

Column 2, line 44, "about-which" should read -- about which --

Column 9, line 52, "Interchnged" should read -- interchanged --

Column 12, line 7, "mounted" should read -- mounting --.

Column 12, line 66, "latch" should be inserted after -- safety --.

Column 13, line 27, delete "extending through the said first terminal portion,"

Column 14, line 1, delete "and defining a support".

Signed and Sealed this

Tenth Day of May, 1988

Attest:

DONALD J. QUIGG

Attesting Officer

Commissioner of Patents and Trademarks